(12) United States Patent
Lee et al.

(10) Patent No.: US 6,833,202 B2
(45) Date of Patent: Dec. 21, 2004

(54) ELECTROLUMINESCENT DEVICES

(75) Inventors: Shuit-Tong Lee, Hong Kong (CN);
Chun-Sing Lee, Hong Kong (CN);
Peng-Fei Wang, Ma On Shan (CN);
Zhi-Yuan Xie, Changchun (CN)

(73) Assignee: City University of Hong Kong, Hong Kong (CN)

( * ) Notice: Subject to any disclaimer, the term of this patent is extended or adjusted under 35 U.S.C. 154(b) by 0 days.

(21) Appl. No.: 10/388,151

(22) Filed: Mar. 13, 2003

(65) Prior Publication Data
US 2004/0180234 A1 Sep. 16, 2004

(51) Int. Cl.[7] .................. C09K 11/06; H05B 33/14; C07D 455/00
(52) U.S. Cl. .................. 428/690; 428/917; 313/504; 313/506; 546/94; 252/301.16
(58) Field of Search .................. 428/690, 917; 313/504, 506; 546/94; 252/301.16

(56) References Cited

U.S. PATENT DOCUMENTS

| | | | | |
|---|---|---|---|---|
| 3,912,724 A | * | 10/1975 | Begland | 546/188 |
| 3,962,220 A | * | 6/1976 | Begland | 548/455 |
| 3,962,221 A | * | 6/1976 | Begland | 548/455 |
| 4,002,616 A | * | 1/1977 | Neumer | 548/455 |
| 4,265,632 A | * | 5/1981 | Papenfuhs et al. | 8/512 |
| 5,935,720 A | | 8/1999 | Chen et al. | 428/690 |
| 6,486,110 B2 | * | 11/2002 | Bachmann et al. | 510/311 |
| 2001/0004780 A1 | * | 6/2001 | Mach et al. | 8/478 |

FOREIGN PATENT DOCUMENTS

WO    WO 02/22760 A1 * 3/2002
WO    WO 200257537 A * 7/2002

OTHER PUBLICATIONS

Vijayalakshmi et al., "DNA Cleavage by a Chromium (III) Complex", Biochemical and Biophysical Research Communications, vol. 271, Issue 3, May 19, 2000, pp. 731–734.*
Chemistry of Materials, (1996), vol. 8, pp. 541–545.*
Chemical Communications, Jun. 30, 2003, vol. 14, pp. 1664–1665, (abstract).*
Synthetic Metals, vol. 115, (2000), pp. 191–196.*
Makromolekulare Chemie, 184(4), pp. 763–778, (1983).*
Polymer Bulletin, vol. 13, No. 1, pp. 57–64, (1985).*
Pure and Applied Optics 5(5), pp. 603–612, (1996).*
Inorganic Chemistry, (1996), vol. 35, pp. 5492–5499.*

(List continued on next page.)

Primary Examiner—Dawn Garrett
(74) Attorney, Agent, or Firm—Heslin Rothenberg Farley & Mesiti P.C.

(57) ABSTRACT

Organic electroluminescence devices are described, each of which comprises an anode, a cathode, a luminescent layer, at least one hole-transporting layer disposed between the anode and the luminescent layer, at least one electron-transporting layer disposed between the cathode and the luminescent layer, and a substrate present on either the anode or cathode. The luminescent layer in the devices uses as red-emitting materials, salicylaldiminato Schiff bases or their metal complexes based on diaminomaleonitrile and salicylaldehyde derivatives. These organic electroluminescence devices exhibit excellent color chromaticity co-ordinates and good efficiency.

39 Claims, 1 Drawing Sheet

OTHER PUBLICATIONS

J.L. Segura, "The Chemistry of Electroluminescent Organic Materials," *Acta Polym.* 49, 319–44 (1998).

C.W. Tang and S.A. Van Slyke, "Organic Electroluminescent Diodes," *Appl. Phys. Lett.*, 51 (12), 913–15 (1987).

C.H. Chen et al., "Recent Developments in Molecular Organic Electroluminescent Materials," *Macromol. Symp.* 125, 1–48 (1997).

U. Mitschke and P. Bäuerle, "The Electroluminescence of Organic Materials," *J. Mater. Chem.* 10, 1471–1507 (2000).

Y. Shirota, "Organic Materials for Electronic and Optoelectronic Devices," *J. Mater. Chem.* 10, 1–25 (2000).

U.S. application Ser. No.: 10/229,493, Filed Aug. 28, 2002, "Electroluminescence Devices Using Pyrazolo [3,4b] Quinoxaline Derivatives."

U.S. application Ser. No.: 10/357,616, Filed Feb. 04, 2003 "Electroluminescent Devices."

* cited by examiner

ELECTROLUMINESCENT DEVICES

CROSS REFERENCE TO RELATED APPLICATION

This application is related to copending U.S. patent application Ser. No. 10/357,616, filed Feb. 4, 2003, entitled "Electroluminescent Devices".

FIELD OF THE INVENTION

The present invention relates to organic electroluminescence (EL) devices, more particularly to electroluminescence devices comprising red light emitting materials using bissalicylaldiminato Schiff Bases and their metal complexes for thin-film type organic electroluminescence devices.

BACKGROUND OF THE INVENTION

In 1960s, many trials for the preparation of organic electroluminescence devices were reported by using conjugated materials generally having fused aromatic rings (U.S. Pat. No. 3,172,862, issued 1965; U.S. Pat. No. 3,173,050, issued 1965). However, the efficiencies and lifetimes of these organic EL devices were much lower than those obtained from inorganic systems, therefore research activities were mainly focused on inorganic materials.

The reason for the low luminance of the early organic EL devices was the highly resistive EL medium, which prevented efficient injection of carriers into the light-emitting layer. Tang and VanSlyke solved this problem successfully in the 1980s (Tang and VanSlyke, Appl. Phys. Lett., 1987, 51, 913), improving significantly the performance of organic EL devices by using a two-thin-layer device with a hole-transporting layer of an organic substance laminated on an organic emitting layer. This work revived the research on organic EL devices, and resulted in the development of a new generation of light-emitting diodes with organic dyes.

Since then, many efforts have been made to further improve the properties of such EL devices, such as efficiency, stability and color purity (U.S. Pat. Nos. 5,141,671; 4,539,507; 6,020,078; 5,935,720; 5,972,247; 5,593,788; 4,885,211; 5,059,862; 5,104,740; 5,069,975; 5,126,214; 5,389,444; 6,165,383; 6,245,449; Chen et al, Macromol. Symp., 1997, 125, 1; Segura, Acta. Polym., 1998, 49, 319; Mitschke and Bauerle, J. Mater. Chem., 2000, 10, 1471). Among these, one of the most convenient and useful methods is to dope a strong emitting material into a host material to form a guest-host system. Thus, in principle, an organic EL device with good efficiency, high stability, as well as the desired color with proper chromaticity can be obtained by doping different strongly emitting materials into a host material such as tri-(8-hydroxyquinolinato)aluminum ($AlQ_3$) to meet the requirement of practical applications.

In such a system, as a general rule the energy gap between the lowest unoccupied molecular orbital (LUMO) and the highest occupied molecular orbital (HOMO) of a host material should be larger than that of the doped guest material to allow efficient energy transfer from the host to guest. By using this method, different colors can be achieved to meet the requirement for full-color applications.

It is generally understood that RGB (red-green-blue) materials with good color purity and high efficiency are essentially required for full-color applications. Extensive studies in the past decade have produced efficient blue and green materials which meet the requirement of commercial OLED applications. However, satisfactory red materials with good color purity, high efficiency and good stability are still lacking.

Although many red fluorescent dyes have been tested (Chen et al, Thin solid Films 2000, 363, 327; Chen et al, J. Phys. D. Appl. Phys. 2001, 34, 30; Picciolo et al, Appl. Phys. Lett. 2001, 78, 2378) and red phosphorescent dyes have recently been introduced (O'Brien et al, Appl. Phys. Lett. 1999, 74, 442), there is still an acute need for further improvement. For example, the color purity and efficiency of 4-(dicyano methylene)-2-t-butyl-6-(1,1,7,7-tetramethyljulolidyl-9-enyl)-4H-pyran (DCJTB), a current state-of-the-art red dopant, are still not satisfactory (see Chen et al, Thin solid Films 2000, 363, 327 and Chen et al, J. Phys. D. Appl. Phys. 2001, 34, 30).

Although rare-earth complexes have good color purity, their efficiency and chemical stability fall short of the requirements for commercial applications. Significant advances have recently been achieved using triplet emitters to obtain very efficient red devices. However, due to the long lifetime of triplet states, the density of triplet states can be easily saturated for high brightness applications. As a result, the efficiency of the triplet red emitters decreases rapidly with increasing brightness. This poses a serious problem for applications that require high excitation density such as in a passive dot-matrix display. Thus, new red dyes with high emission quantum yield, saturated red emission, and high stability are still much in demand.

For red-emitting materials, in general, two kinds of compounds are potentially good candidates: (1) compounds with large fused homo-aromatic rings; (2) intramolecular charge transfer (ICT) compounds with electron donating (D) groups and electron withdrawing groups (A) linked by conjugated structure. Since the fused homo-aromatic compounds with a large conjugated structure, especially those which emit in red, are often oxidised easily by singlet oxygen at ambient condition, this series of compounds is not expected to be suitable dopants unless the devices are used under dark conditions or without oxygen. Compared with the fused homo-aromatic compounds, ICT compounds have the following advantages:

[i] their emission wavelengths can easily be tuned by changing substituents to get different colors;

[ii] their molecular structures are relatively easy to modify for desired properties;

[iii] their Stokes shifts are generally large to prevent self-re-absorption efficiently, especially in the solid state;

[iv] they are chemically stable, and are not easily oxidised by singlet oxygen.

Given these advantages, intramolecular charge transfer (ICT) compounds are considered to be potential candidates for use as red-emitters. In particular, donor-acceptor-donor (D-A-D) type ICT compounds are useful as red-emitting materials for organic LEDs. The rationale is that D-A-D type ICT compounds often show desirable properties, aside from the general features of typical D-A type ICT compounds mentioned above. It is generally considered, albeit not well proven, that the fluorescence quantum yield of a D-A-D type ICT compound is higher than that of a D-A ICT compound with the same donor/acceptor moiety and conjugate structure. Moreover, symmetric D-A-D ICT compounds generally show better thermal stability and higher Tg than their D-A counterparts.

Salicylaldiminato Schiff bases are classical ligands for complexation with transition metals such as $Cu^{2+}$, $Ni^{2+}$, $Co^{2+}$, $Zn^{2+}$, $Mn^{2+}$, $Fe^{2+}$ etc. Many salicylaldiminato Schiff bases and their metal complexes have been prepared and are well documented. Recently, salicylaldiminato Schiff bases with intramolecular charge transfer property based on diaminomaleonitrile and p-diethylaminosalicylaldhyde have been used as DNA cleavage and non-linear optical (NLO) materials (Lacroix et al, I. Chem. Mater. 1996, 8, 541; Bella et al, J. Am. Chem. Soc. 1997, 119, 9550). However, these materials have not been tested or used in organic EL devices.

SUMMARY OF THE INVENTION

The object of the present invention is to provide new organic electroluminescence devices which address some of the problems discussed above. In particular, it is an object of the invention to provide organic EL devices with pure saturated red emission, and with a narrow emission band.

The present invention provides an organic electroluminescence device comprising an anode, a cathode, a luminescent layer, at least one hole-transporting layer disposed between the said anode and said luminescent layer, at least one electron-transporting layer disposed between said cathode and said luminescent layer, and a substrate present on either the anode or cathode, wherein the luminescent layer comprises a compound of formula [I]:

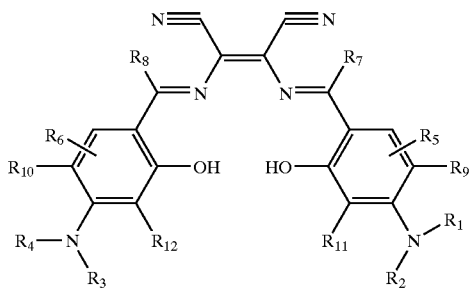

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups;

either $R_9$ and $R_{11}$ are both hydrogen and $R_1$ and $R_2$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_1$ and $R_9$, and $R_2$ and $R_{11}$ each, together with the interjacent carbon and nitrogen atoms, form an optionally substituted ring having between 5 and 7 ring atoms; and either $R_{10}$ and $R_{12}$ are both hydrogen and $R_3$ and $R_4$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_3$ and $R_{12}$, and $R_4$ and $R_{10}$ each, together with the interjacent carbon and nitrogen atoms, form an optionally substituted ring having between 5 and 7 ring atoms; or a metal complex equivalent thereof.

The invention also provides the use of a compound of formula [I], as described above, as a luminescent material in an electroluminescence device. There is further provided a method of using a compound of formula [I] in an electroluminescence device, the method comprising providing a compound of formula [I], and incorporating said compound as a luminescent material within an electroluminescence device which further comprises an anode, a cathode, a hole-transporting layer and an electron-transporting layer.

The invention further provides a compound of formula [I], as described above, with the proviso that the compound of formula [I] is not 2,3-bis-[[(2-hydroxy-4-diethylamino)phenyl](methylene)]-amino]-2-butenedinitrile or the copper, nickel or zinc complex thereof.

The electroluminescence devices of the intention have excellent color chromaticity co-ordinates and good efficiency, and can emit in red. Furthermore, the materials provided by the present invention are eased to synthesise and purify in high yields, thereby being very attractive from an economic perspective, and, when the materials are present as dopants within a host material, have electroluminescence spectra which do not change with doping concentration.

DETAILED DESCRIPTION OF THE INVENTION

Figure 1:
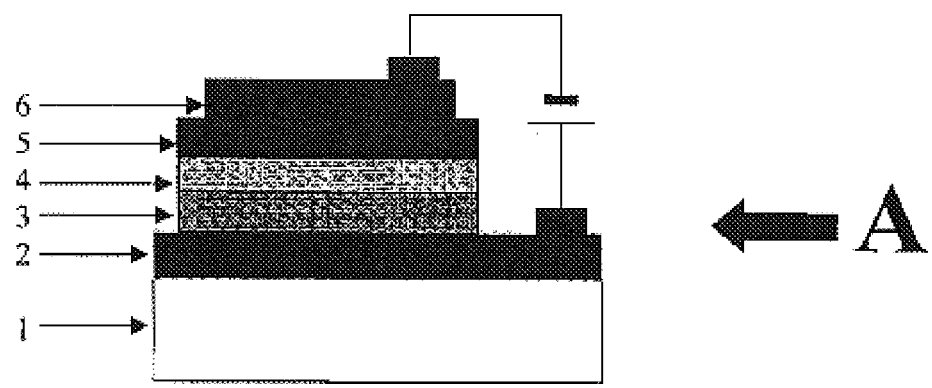
FIG. 1 shows an organic electroluminescence device according to the present invention.
Figure 2:
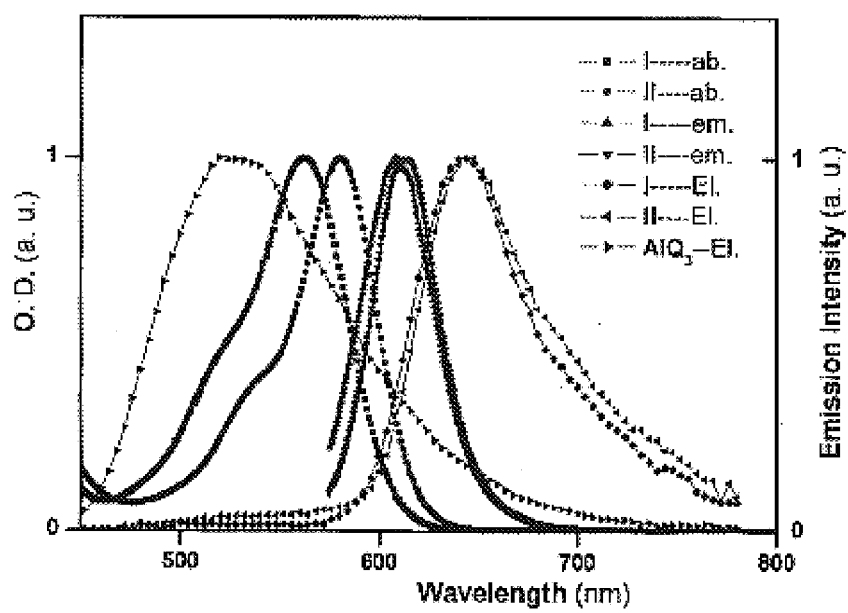
FIG. 2 shows the absorption, emission and electroluminescent spectra in solution of BDPMB (labelled I) and BDPMB-Zn (labelled II) used in the devices of the invention, as well as the electroluminescent spectrum of $AlQ_3$.

Unless otherwise stated in the following description, the term alkyl represents an alkyl group containing from 1 to 18, preferably 1 to 10, and more preferably 1 to 6, carbon atoms. Particularly preferred alkyl groups include methyl, ethyl, propyl, butyl, sec-butyl, tert-butyl, pentyl, hexyl, heptyl, octyl and stearyl.

The terms alkenyl and alkynyl represent alkenyl and alkynyl groups respectively having from 2 to 18, preferably from 2 to 10, and more preferably from 2 to 6 carbon atoms.

The term halogen represents a chlorine, fluorine, bromine or iodine atom, with chlorine and fluorine being preferred. A group containing a halogen atom, e.g. haloalkyl, may contain one or more of these halogen atoms.

Haloalkyl represents any alkyl group substituted by one or more halogen atoms. Preferably haloalkyl represents trichloromethyl or trifluoromethyl.

Hydroxyalkyl represents an alkyl group substituted with at least one hydroxy group. The alkyl group preferably has from 1 to 4 carbon atoms.

Aryl represents a cyclic hydrocarbon having at least one aromatic ring, and having from 5 to 30, preferably from 6 to 14, carbon atoms. Aryl preferably represents a group selected from the group consisting of phenyl, biphenyl, triphenyl, tetraphenyl, o-tolyl, m-tolyl, p-tolyl, o-xylyl, m-xylyl, p-xylyl, or o-cumenyl, m-cumenyl, p-cumenyl and styryl.

The term alkoxy represents an alkyl group linked via an oxygen atom. Preferably alkoxy represents methoxy, ethoxy, propoxy, butoxy, sec-butoxy, tert-butoxy or stearyloxy. Similarly, the terms alkenyloxy and aryloxy represent alkenyl and aryl groups respectively linked via an oxygen atom. Preferably aryloxy represents phenoxy.

Alkylamino represents any amino group of formula —$NH_2$, —NHR' or —NRR' where R and R' are alkyl groups, preferably having from 1 to 10, more preferably from 1 to 4, carbon atoms. Preferred amino groups are —NH$_2$, methyl amino (i.e. —NHMe), ethyl amino, propyl amino, butyl amino, sec-butyl amino, tert-butyl amino, pentyl amino, hexyl amino, heptyl amino, octyl amino, stearyl amino, dimethyl amino (i e. —NMe$_2$), diethyl amino, dipropyl amino, dibutyl amino, disec-butyl amino, ditert-butyl amino, dipentyl amino, dihexyl amino, diheptyl amino, dioctyl amino and distearyl amino.

Arylamino represents any amino group of formula —NHR" or —NHR"R'" where R is an aryl group as defined above. The aryl group is preferably selected from the group consisting of phenyl, naphthyl, anthryl and tolyl. Preferred arylamino groups include phenylamino, diphenylamino, phenylnaphthylamino, phenylanthrylamino, o-tolylnaphthylamino, p-tolylnaphthylamino, m-tolylnaphthylamino, o-tolylanthrylamino, p-tolylanthrylamino, m-tolylanthrylamino and naphthylanthrylamino.

Alkylthio represents an alkyl group linked by a sulphur atom. Preferred alkylthio groups include methylthio, ethylthio, propylthio, butylthio, sec-butylthio and tert-butylthio. Similarly, arylthio represents an aryl group linked by a sulphur atom. Preferably arylthio represents phenylthio.

The term ester represents a group of formula —C(O)OR where R is a hydrogen atom or an alkyl group. Preferably the alkyl group has from 1 to 6, more preferably from 1 to 4, carbon atoms.

Siloxy represents a group of general formula —OSiR$_3$, where each R group is independently selected from the group consisting of a hydrogen atom and an alkyl group. The alkyl group preferably has from 1 to 6, more preferably 1 to 4, carbon atoms.

Cyclic hydrocarbon represents both mono- and polycyclic hydrocarbons, which may be saturated or unsaturated, having from 3 to 20, more preferably from 3 to 10, carbon atoms. Preferred cyclic hydrocarbons include mesityl, pentarhenyl, indenyl, naphthyl, azulenyl, heptalenyl, acenaphtylenyl, phenalenyl, fluorenyl, anthryl, anthraquinonil, phenantolyl, pyrenyl, crysenyl, picenyl, rebicenyl and trinaphthylenyl.

The term heterocyclic represents groups having between 3 and 20, more preferably between 3 and 10, carbon atoms and having one or more 4, 5, 6 or 7 member saturated or unsaturated rings containing 1, 2 or 3 oxygen, nitrogen or sulphur atoms. Preferred heterocyclic groups include pyranthrenyl, oparenyl, thienyl, furyl, pyrrolyl, imidazolyl, pyrazolyl, pyridyl, pylazinyl, pyrimidinyl, pyridazinyl, indolyl, quinolyl, isoquinolyl, phthalazinyl, quinoxalynyl, quinazolynyl, carbazolyl, acrydinyl, phenadinyl, furluryl, isochiazolyl, isothiazolyl, isoquixazolyl, furazanyl, phenoquisadinyl, benzthiazolyl, benzoxazlyl and benzoimidazolyl.

Mercapto represents the group —SH.

Carbonyl represents a group having the general formula —C(O)R, where R is a hydrogen atom or an alkyl group. The alkyl group preferably has from 1 to 6, more preferably 1 to 4, carbon atoms.

Sulfone represents a group having the general formula —SO$_2$R, where R is a hydrogen atom or an alkyl group. The alkyl group preferably has from 1 to 6, more preferably 1 to 4, carbon atoms.

When any of the groups listed above are described as optionally substituted, the substituent groups include halogen atoms, hydroxy, cyano, amino, nitro, alkyl, cyclic hydrocarbon, haloalkyl, alkoxy, haloalkoxy, carboxyl, alkylthio, alkylamino, arylamino, ester, siloxy, aryl, aryloxy, alkenyl, alkenyloxy and alkynyl, as well as cyclic hydrocarbon and heterocyclic groups. Preferred optional substituents include alkyl, haloalkyl, aryl, alkoxy, aryloxy, alkylamino, arylamino, alkylthio, arylthio, ester, siloxy, cyclic hydrocarbon and heterocyclic groups, with alkyl groups being particularly preferred.

The components of the electroluminescence device of the present invention will now be described individually in more detail.

Substrate

The substrate is used as a support for the organic electroluminescence device of the present invention. It preferably consists of a quartz or glass sheet, a metal sheet or foil, or a plastic film or sheet. However, the most preferred materials are glass sheet or transparent synthetic resin such as polyester, polycarbonate, and polysulfone. The substrate can be in contact with the anode, or alternatively can be in contact with the cathode.

Anode and Cathode

The anode may comprise any suitable material known in the art, and usually comprises a metal such as silver, gold, aluminum, nickel or palladium; a metal oxide such as an oxide of indium and/or tin; carbon black or a conductive resin such as poly(3-methylthiophene).

The materials mentioned above for making the anode may also be employed for preparation of the cathode. However, the preferred material for the cathode is a metal having a low work function, which is favourable to the efficient injection of electrons. Thus, a suitable metal such as magnesium, aluminum, silver and indium, or alternatively their alloys may be used.

The method for preparing the anode and the cathode may be any conventional technique known in the art, but is preferably vacuum deposition or sputtering. However, when the material is in the form of fine particles of a metal, carbon black, a metal oxide or a conductive resin powder, it can be dispersed into a suitable binder resin in solution and coated onto a substrate to form the electrodes. Furthermore, in the case of a conductive resin, a thin film may be formed directly on a substrate by electrolytic polymerization.

The anode or cathode can be made to have a multi-layered structure by depositing layers of the different materials mentioned above. However, preferably at least one of the electrodes has a transmittance of visible light of at least 60%, more preferably at least 80%. In this respect, this layer should not be too thick, generally from 5 to 1,000 nm, more preferably from 10 to 500 nm.

Hole-transporting Layer

An organic hole-transporting layer is located on the anode, and comprises a compound which is able to transport holes efficiently from the anode to the organic emitting layer between the electrodes to which an electric field is applied. Therefore, such a compound is required to have a high efficiency of injecting holes from the anode, to be capable of efficiently transporting the injected holes to an emitting layer or an emitting material, to prevent the migration of excitons generated in an emitting layer into an electron injecting zone or an electron transporting material, and to be capable of forming a thin film. Thus, a suitable hole-transporting compound should usually have a low ionisation potential, high hole mobility and good stability. Moreover, the impurities likely to form traps should be minimised during preparation or use.

The compounds, which can be used together or independently as a hole-transporting material, include those disclosed in U.S. Pat. No. 5,935,720, aromatic tertiary amines, phthalocyanine derivatives, naphthalocyanine derivatives, porphyrin derivatives, pyrazoline derivatives, carbazole derivatives, benzidine type triphenylamine, diamine type triphenylamine, derivatives of these, and polymer materials such as polyvinylcarbazole and polysilane.

Hole-transporting materials which can be effectively used in the organic electroluminescence device of the present invention include aromatic tertiary amine derivatives. Some particularly useful hole-transporting materials include:

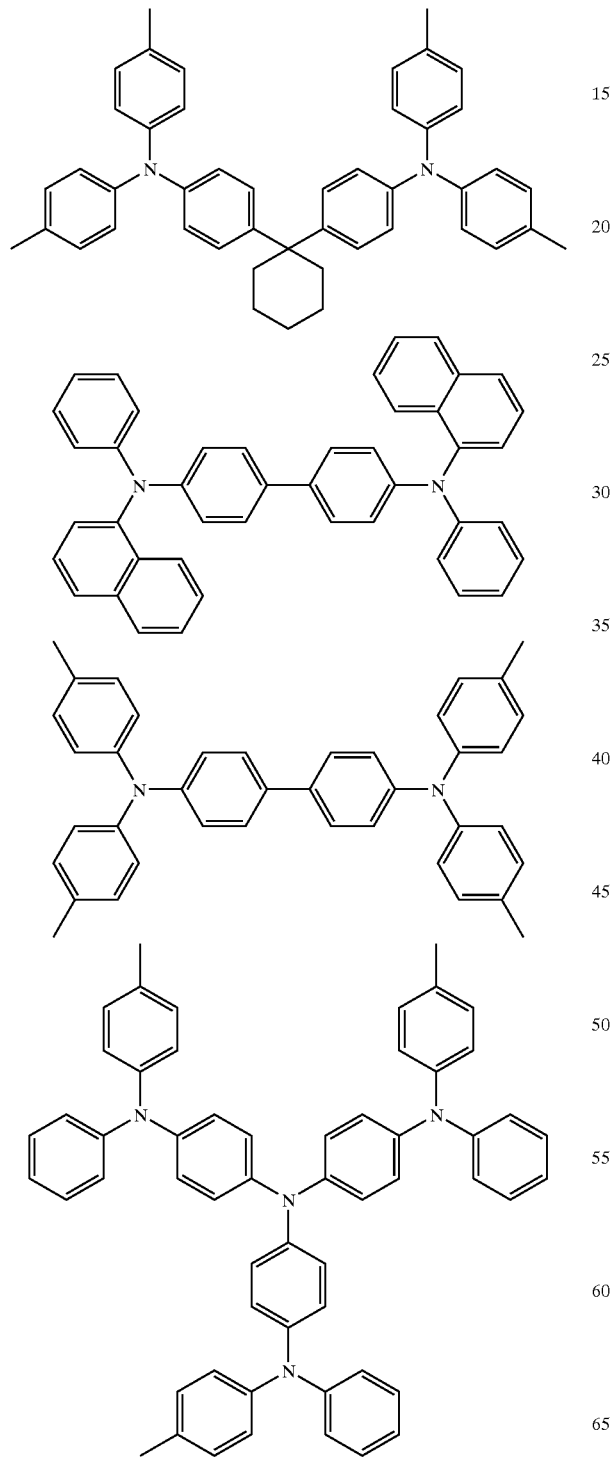

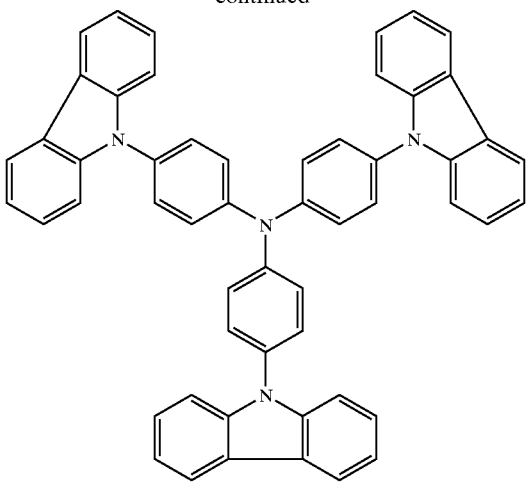

The materials mentioned above are applied to the anode by any conventional method, but are preferably laminated onto the anode by vacuum deposition or a coating/casting method to form the hole transport layer of the present invention. This hole-transporting layer usually has a thickness from 5 to 400 nm, preferably from 30 to 100 nm. In order to obtain a uniformly thin film, the vacuum deposition method is preferred.

Electron-transporting Layer

The electron-transporting layer comprises an electron-transporting material which is such that electrons can be injected from the cathode easily; the mobility of transporting electrons is excellent; and the excitons generated in the light-emitting layer into hole injection zone is blocked. Moreover, a good capability for forming a thin film is also desirable.

Such an electron transport material generally has a large electron affinity, for example, thiopyrandioxide derivatives, perylene tetracarboxylic acid derivatives, oxadiazole derivatives, metal complexes of 8-hydroxyquinoline, 10-hydroxybenzo[h]quinoline, pyrrolopyridine derivatives and naphthylidine derivatives. Examples are shown as follows:

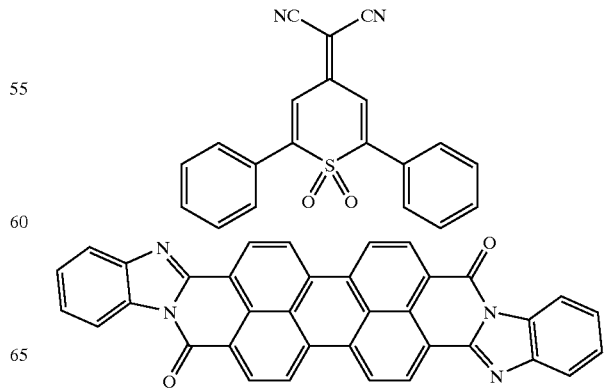

-continued

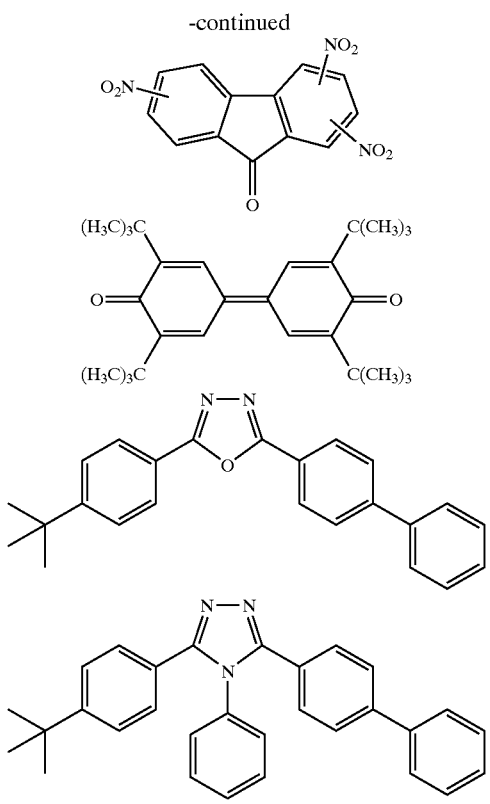

The electron-transporting layer can be formed by any conventional method, but is preferably formed by vacuum deposition or a coating/casting method. This electron-transporting layer usually has a thickness of from 5 to 400 nm, preferably from 30 to 100 nm. In order to obtain a uniformly thin film, the vacuum deposition method is more preferable.

Luminescent Layer

The luminescent, or light-emitting, layer comprises a compound of formula [I]. The compound of formula [I] may be present as its metal complex equivalent, for example with the metal being selected from the group consisting of Mg, Ca, Ba, Cr, Fe, Ni, Cu and Zn. Zinc is particularly preferred.

In one embodiment, groups $R_9$ to $R_{12}$ of [I] are all hydrogen atoms, thus giving a compound of general formula [II]:

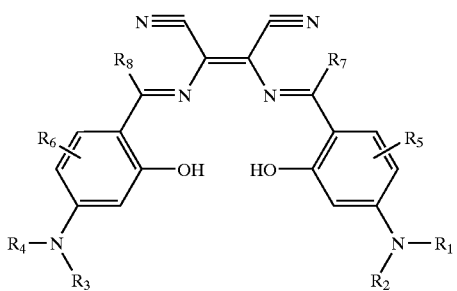

[II]

or a metal complex equivalent thereof. It is preferred that the groups $R_1$ to $R_4$ are independently selected from the group consisting of hydrogen, alkyl, aryl and haloalkyl, with hydrogen being most preferable. Similarly, while groups $R_5$ to $R_8$ are preferably independently selected from hydrogen, alkyl, alkoxy, aryl, aryloxy and haloalkyl, it is preferred that they are all hydrogen atoms.

As discussed above, the compound of general formula [I] may be present as its metal complex equivalent. Thus, in another embodiment of the invention the luminescent layer comprises a compounds of formula [III]:

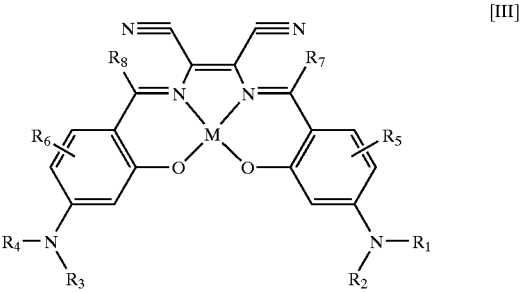

[III]

where M is a metal atom.

In this embodiment, $R_5$ to $R_8$ are preferably independently selected from hydrogen, alkyl, aryl and haloalkyl, with hydrogen being preferred.

In an alternative embodiment, the groups $R_1$ and $R_9$, $R_2$ and $R_{11}$, $R_3$ and $R_{12}$, and $R_4$ and $R_{10}$, together with the interjacent carbon and nitrogen atoms, may independently form optionally substituted rings having between 5 and 7 ring atoms. It is preferred that the rings have 6 ring atoms.

The groups $R_1$ and $R_9$, $R_2$ and $R_{11}$, $R_3$ and $R_{12}$, and $R_4$ and $R_{10}$ may form different carbon-nitrogen rings. For example $R_1$ and $R_9$ may, together with the interjacent atoms, form a six-membered ring, while $R_2$ and $R_{11}$ may independently, together with the interjacent atoms, form a five-membered ring. Alternatively, $R_1$ and $R_9$ may, together with the interjacent atoms, form a six-membered ring, while $R_2$ and $R_{11}$ may not form a ring at all, but instead may represent terminal groups. However, it is preferable that $R_1$ represents the same group as $R_2$, $R_3$ represents the same group as $R_4$, $R_9$ represents the same group as $R_{11}$, and $R_{10}$ represents the same group as $R_{12}$. It is particularly preferred that $R_1$ to $R_4$ represent the same group, and $R_9$ to $R_{12}$ represent the same group.

The rings which may be formed by $R_1$ to $R_4$ and $R_9$ to $R_{12}$ may be optionally substituted, for example with the substituents being selected from the group consisting of alkyl, haloalkyl, hydroxy, aryl, alkoxy, aryloxy, alkylamino, arylamino, alkylthio, arylthio, ester, siloxy, cyclic hydrocarbons and heterocyclic groups. The substituent groups are preferably short chain groups, for example having between 1 and 4 atoms. Particularly preferred are $C_1$ to $C_4$ alkyl groups, and in particular methyl groups. While any number of substituents can be present, it has been found that a particularly preferred substitution pattern is where the ring or rings are di-substituted, preferably with methyl groups. The two substituent groups may be present on different ring atoms, although it is preferred that the same ring atom bears both substituents. In the case of a 6-membered ring, it is preferred that the two substituents are present on the ring atoms which is para to the nitrogen atom.

Thus, a particularly preferred compound has the formula [IV]:

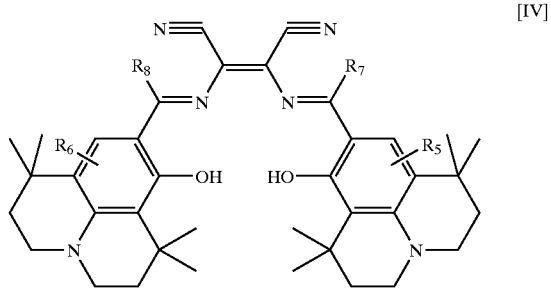

or a metal complex equivalent thereof.

If the compound is present as its metal complex equivalent, it therefore has the formula [V]:

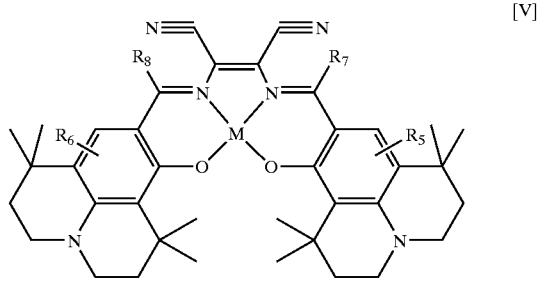

When the luminescent layer has the general formula [IV] or [V], it is preferred that $R_5$ to $R_8$ are independently selected from the group consisting of hydrogen, alkyl, haloalkyl, aryl, aryloxy and alkoxy, with hydrogen atoms being most preferred.

The compounds of formula [I] are produced according to synthetic methods which would be apparent to the person skilled in the art, and an exemplary method is described in Examples 1 and 2 below. While the compounds of formula [I] need not be symmetrical about the central C=C bond, it is easier to synthesise compounds which are symmetrical. For example, one mole of diaminomaleonitrile can simply be reacted with two moles of an appropriate aldehyde (such as 2-hydroxy-4-diethylaminobenzaldehyde) in order to produce a symmetrical molecule. If an asymmetrical molecule is required, one mole of diaminomaleonitrile would need to be reacted with one mole each of two separate aldehydes.

The electron and hole pair generated in the electroluminescence device recombine in the region of the luminescent layer to produce excitons, which may decay to the ground state in a radiative way, resulting in an emission as either fluorescence or phosphorescence. The luminescent layer material is thus generally required to have a high emission quantum yield, a suitable energy gap, as well as a good ability to form a uniformly thin film. In view of the many requirements of the luminescent layer, this layer may contain other materials, in addition to the compound of formula [I]. For example, the luminescent layer may also comprise a further light emitting material, a dopant, a hole transport material or an electron transport material as required. Particular compounds suitable for use in conjunction with the compound of formula [I] in the luminescent layer include fused aromatic compounds, benzidine type triphenylamine, styrylamine type triphenylamine, diamine type triphenylamine, 8-hydroxyquinolinato metal complexes, or other fluorescence or phosphorescence dyes.

In addition to these other materials, the compound of formula [I] may be used as a dopant within a host emitting material. It is understood that doping strongly luminescent materials into a host emitting material can improve the performance of an organic EL device significantly, with the following advantages:

(i) The electroluminescent efficiency may be improved significantly;

(ii) The color can be tuned by doping different emitting materials;

(iii) The emitting materials with properties of a poor film forming ability and concentration self-quenching can also be used; and (iv) The operational stability of organic EL device can be improved.

Thus, it is preferred that the compound of formula [I] is present as a dopant within a host material. A number of host emitting materials may be used, but the preferred materials are $AlQ_3$, $GaQ_3$ and $InQ_3$, with $AlQ_3$ being particularly preferred.

Other Materials

Other variations and modifications of the devices described above will be apparent to the skilled person, however one particularly preferable embodiment includes a hole injection material disposed between the anode and the hole-transporting layer. This hole injection material enhances hole injection from the anode in the electroluminescence device, and is preferably present in the form of a thin layer. A suitable thickness is about 15 nm. Particularly useful materials include copper phthalocyanine, and the porphyrinic derivatives disclosed in U.S. Pat. No. 5,972,247.

DETAILED DESCRIPTION OF THE DRAWINGS

Representative devices of the invention are depicted in FIG. 1, which shows an organic electroluminescence device structure, A. Reference numeral 1 indicates a substrate, numeral 2 indicates an anode, numeral 3 indicates an organic hole-transporting layer, numeral 4 indicates a luminescent layer, numeral 5 indicates an organic electron-transporting layer and numeral 6 indicates a cathode. A suitable process for manufacturing a device having this structure is given in Example 3 below.

EXAMPLES

The present invention will be explained in more detail with reference to Examples hereinafter. The molecular structures for the specific compounds of formula [I] used in the examples are as follows:

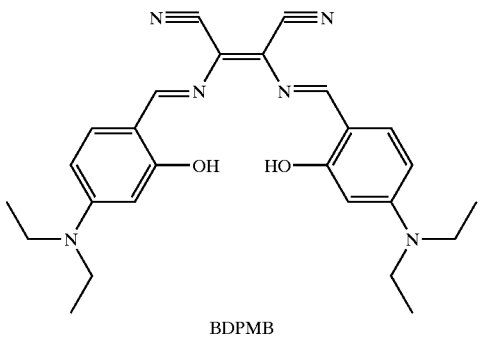

BDPMB

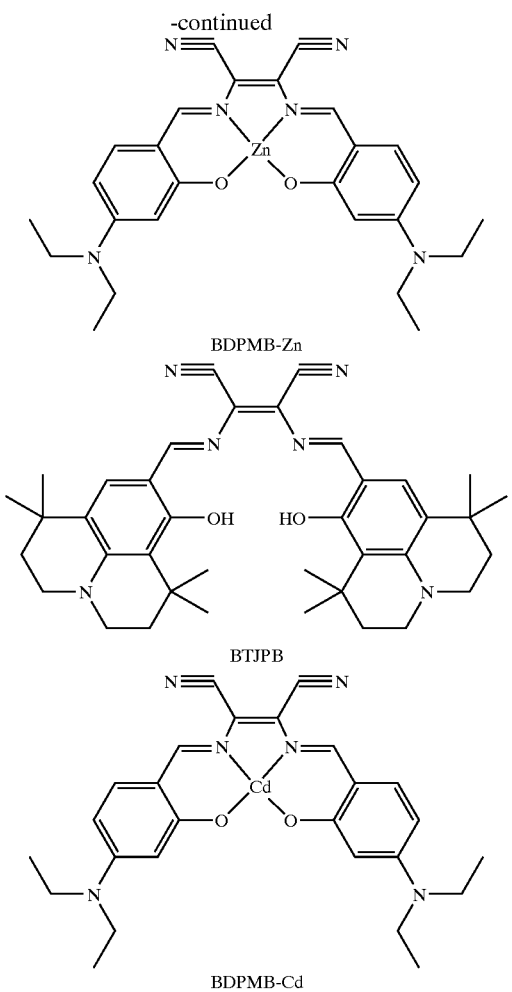

BDPMB-Zn

BTJPB

BDPMB-Cd

Example 1

Synthesis of 2,3-bis[[[(2-hydroxy-4-diethylamino)phenyl](methylene)]amino]-2-butanedinitrile (BDPMB)

To a solution of 0.773 g 2-hydroxy-4-diethylaminobenzaldehyde and 0.216 g diaminomaleonitrile in 20 ml EtOH, was added a drop of concentrated $H_2SO_4$. The mixture was stirred overnight. The green precipitate was filtered and washed with EtOH and $H_2O$, and was then recrystallized from DMF/EtOH to get green needles (BDPMB) 0.73 g. $^1$HNMR (DMSO) 1.09–1.14 (m, 12H), 3.42–3.44 (m, 8H), 6.14 (s, 2H), 6.40–6.43 (d, 2H), 7.53–7.55 (d, 2H), 8.55 (s, 2H). Anal.: Calcd. for $C_{26}H_{30}N_6O_2$: C, 68.10; H, 6.59; N, 18.33. Found: C, 68.27; H, 6.61; N, 18.54. MS: M/z, 458.

Example 2

Synthesis of Zinc Complex of BDPMB (BDPMB-Zn)

To a hot solution of 0.43 g $Zn(CH_3COO)_2 \cdot 3H_2O$ in 300 ml EtOH was added a solution of 0.773 g 2-hydroxy-4-diethylaminobenzaldehyde and 0.216 g diaminomaleonitrile in 100 ml EtOH. The mixture was stirred for two days under reflux. After cooling, the yellow-green precipitate was collected by filtration, washed by EtOH, and dried to get 0.48 g. After purification by recrystallization from DMF/EtOH, and drying, 0.40 g green fine needles (BDPMB-Zn) was obtained. $^1$HNMR (DMSO) 1.09–1.13 (m, 12H), 3.37–3.39 (m, 8H), 5.80 (s, 2H), 6.18–6.22 (d, 2H), 7.12–7.15 (d, 2H), 8.09 (s, 2H). Anal.: Calcd. for $C_{26}H_{28}N_6O_2Zn \cdot H_2O$: C, 57.84; H, 5.60; N, 15.56. Found: C, 57.56; H, 5.33; N, 15.65. MS: M/z, 521($M^{+1}$).

Example 3

Synthesis of Cadmium Complex of BDPMB (BDPMB-Cd)

To a hot solution of 0.36 g $CdCl_2$ in 300 ml EtOH was added a solution of 0.773 g 2-hydroxy-4-diethylaminobenzaldehyde and 0.216 g diaminomaleonitrile in 100 ml EtOH. The mixture was stirred for two days under reflux. After cooling, the yellow-green precipitate was collected by filtration, washed by EtOH, dried to get 0.41 g. After purification by recrystallization from DMF/EtOH and drying, 0.32 g deep-red solid (BDPMB-Cd) was obtained. $^1$HNMR (CDCl$_3$) 1.09–1.13 (m, 12H), 3.16–3.22 (m, 8H), 5.49 (s, 2H), 6.05–6.08 (d, 2H), 6.87–6.90 (d, 2H), 8.17 (s, 2H). Anal.: Calcd. for $C_{26}H_{28}N_6O_2Cd$: C, 54.89; H, 4.96; N, 14.77. Found: C, 54.86; H, 4.95; N, 14.64. MS: M/z, 571 (M+1).

Example 4

Synthesis of 2,3-bis[[(2-hydroxy-1,1,7,7-tetramethyljulolidyl)phenyl](methylene)]amino]-2-butanedinitrile (BTJPB)

To a solution of 0.547 g 8-hydroxy-1,1,7,7-tetramethyljulolidine-carboxaldehyde and 0.108 g diaminomaleonitrile in 15 ml EtOH, was added a drop of concentrated $H_2SO_4$. The mixture was stirred overnight. The black precipitate was filtered and washed with EtOH and $H_2O$, then recrystallized from the DMF/EtOH to get green solid (BTJPB) 0.33 g. $^1$HNMR (CDCl$_3$) 1.27 (s, 12H), 1.53 (s, 12H), 1.71–1.75 (m, 8H), 3.26–3.38 (m, 8H), 6.98 (s, 2H), 8.43 (s, 2H), 12.52 (s, 2H). Anal.: Calcd. for $C_{38}H_{46}N_6O_2$: C, 73.76; H, 7.49; N, 13.58. Found: C, 73.56.27; H, 7.45; N, 13.31. MS: M/z, 619.

Example 5

Method for Fabrication of Electroluminescence Device

An indium-tin-dioxide (ITO) coated glass substrate was sequentially ultra-sonicated in a detergent, rinsed in de-ionized water, exposed to UV light for 20 minutes, and finally dried. A hole transporting layer of N,N'-bis-(1-naphthyl)-N,N'-diphenylbenzidine was deposited on the ITO anode at a vacuum deposition rate of about 15 nm/min using a tantalum boat to form a thickness of 60 nm. A light-emitting layer of $AlQ_3$ doped with a material of formula [I] was then co-deposited onto the hole-transporting layer to a thickness of about 30 nm. The concentration of dopants can be controlled by deposition rate, as required. In the next step, an electron-transporting layer of $AlQ_3$ was deposited onto the light-emitting layer to a thickness of about 30 nm. Then, a cathode consisting of a 10:1 atomic ratio of Mg:Ag and with a thickness of about 200 nm was deposited on to the $AlQ_3$ layer. Finally, the device was hermetically packaged in a dry glove box.

Example 6

An electroluminescence device with 2,3-bis[[(2-hydroxy-4-diethylamino)phenyl](methylene)]amino]-2-butanedinitrile (BDPMB) doped $AlQ_3$ as the light-emitting layer was fabricated using the same procedure as described in Example 5. The device structure can therefore be summarised as follows: ITO/NPB(60 nm)/$AlQ_3$: Dopant(30 nm)/$AlQ_3$(30 nm)/MgAg(200 nm), where BDPMB is the dopant, and is present at a concentration of 1 wt %. The light emission characteristics are shown in Table 1. The properties of DCJTB are shown for comparison.

Example 7

The electroluminescence device with Zinc complex (BDPMB-Zn) doped AlQ$_3$ as the light-emitting layer was fabricated using the same procedure as described in Example 5. The device structure is therefore the same as given in Example 6 above, but using BDPMB-Zn as the dopant. The light emission characteristics are shown in Table 1.

Example 8

The electroluminescence device with Cadmium complex (BDPMB-Cd) doped AlQ$_3$ as the light-emitting layer was fabricated using the same procedure as Example 5.

Example 9

The electroluminescence device with BTJPB doped AlQ$_3$ as the light-emitting layer was fabricated using the same procedure as Example 5.

TABLE 1

Electroluminescent data for electroluminescence devices comprising the compounds of Examples 1 to 4, including maximum luminance ($L^{max}$), efficiency ($\eta$) and emission peaks, as well as CIE co-ordinates at room temperature, recorded in acetonitrile.

| Compounds | Voltage (V) | $L^{max}$ (cd/m$^2$) | $\eta$ (cd/A) | $\lambda^{El}$ (nm) | C.I.E. (x, y) |
|---|---|---|---|---|---|
| BDPMB | 12.5 | 620 | 0.55 | 641 | 0.65, 0.32 |
| BDPMB-Zn | 15.5 | 1560 | 0.51 | 645 | 0.67, 0.32 |
| BDPMB-Cd | 14.5 | 2100 | 0.43 | 642 | 0.66, 0.32 |
| BTJPB | 13.5 | 1736 | 0.48 | 651 | 0.67, 0.37 |
| DCJTB | 9.2 | 378[a] | 1.89 | — | 0.625, 0.37 |

[a]Dopant concentration: 1% at 20 mA/cm$^2$.

From Table 1 it can be seen that all devices of the invention show saturated red emission with excellent color chromaticity co-ordinates. For example, the power efficiency is 0.55 cd/A for BDPMB, which is high for saturated red emission with CIE co-ordinates (x=0.65, 0.32) which are well matched to the desired range of the color gamut used for color television.

The compounds exhibited red emission in acetonitrile with maximum emissions at about 610 nm, and only show slight shift of the emission peaks with increasing solvent polarity in the range between the middle to strong polar solvents. It is worth noting that the fluorescence quantum yields ($\Phi_f$) of compounds used in the invention are very high in a strong polar solvent like acetonitrile. The values are in fact much higher than that for one of the most important red dopants, DCJTB, which has a value of 0.12 in the same solvent. In a middle polar solvent such as dichloromethane (DCM) the fluorescence quantum yields are comparable.

From the examples above, it is evident that saturated red-emitting electroluminescence devices with excellent color chromaticity co-ordinates and high power efficiencies can be obtained in accordance with the teachings of the invention. The luminescent layers tested proved to be efficient red-emitting materials for organic electroluminescence devices with excellent color chromaticity co-ordinates and good efficiency. Moreover, the compounds disclosed here have an additional feature of highly fluorescent, narrow saturated red emission band, as well as ease of synthesis. Thus, it is desirable to use these salicylaldiminato Schiff bases and their metal complexes based on diaminomaleonitrile and salicylaldehyde derivatives as red-emitting materials to achieve organic electroluminescence devices with excellent color chromaticity co-ordinates and good efficiency.

The foregoing is offered primarily for the purposes of illustration. It will be readily apparent to those skilled in the art that numerous variations, modifications and substitutions may be made in the materials, procedural steps and conditions described herein without departing from the spirit and scope of the invention.

We claim:

1. An organic electroluminescence device comprising an anode, a cathode, a luminescent layer, at least one hole-transporting layer disposed between said anode and said luminescent layer, at least one electron-transporting layer disposed between said cathode and said luminescent layer, and a substrate present on either the anode or cathode, wherein the luminescent layer comprises a compound of formula [I]:

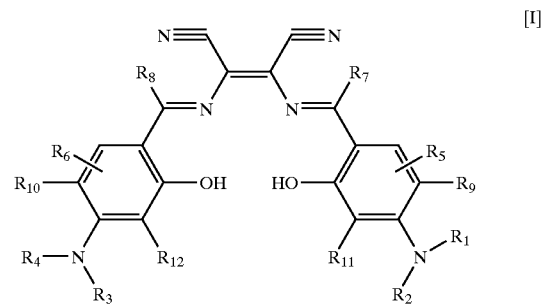

wherein R$_5$–R$_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, with the proviso that R$_7$ and R$_8$ are not both hydrogen atoms;

either R$_9$ and R$_{11}$ are both hydrogen and R$_1$ and R$_2$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or R$_1$ and R$_9$, and R$_2$ and R$_{11}$ each, together with the interjacent carbon and nitrogen atoms, form an optionally substituted ring having between 5 and 7 ring atoms; and either R$_{10}$ and R$_{12}$ are both hydrogen and R$_3$ and R$_4$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or R$_3$ and R$_{12}$, and R$_4$ and R$_{10}$ each, together with the interjacent carbon and nitrogen atoms, form an optionally substituted ring having between 5 and 7 ring atoms;

or a metal complex equivalent thereof.

2. The device of claim 1 wherein the compound of formula [I] is present as a dopant within a host material selected from the group consisting of AlQ$_3$, GaQ$_3$ and InQ$_3$.

3. The device of claim 2 wherein the host material is AlQ₃.

4. The device of claim 1 additionally comprising a hole injection material disposed between the anode and the hole-transporting layer.

5. The device of claim 4 wherein the hole injection material comprises copper phthalocyanine or a porphyrinic derivative.

6. An organic electroluminescence device comprising an anode, a cathode, a luminescent layer, at least one hole-transporting layer disposed between said anode and said luminescent layer, at least one electron-transporting layer disposed between said cathode and said luminescent layer, and a substrate present on either the anode or cathode, wherein the luminescent layer comprises a compound of formula [I] present as its metal complex equivalent, with the metal being selected from the group consisting of Mg, Ca, Ba, Cr, Fe, Co, Ni, Cu and Zn

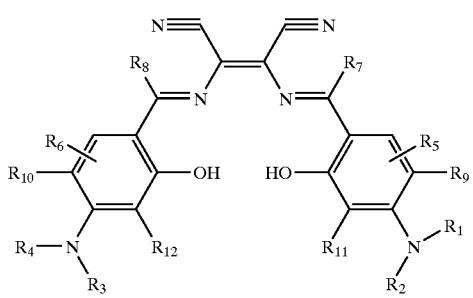

[I]

wherein R₅–R₈ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups;

either R₉ and R₁₁ are both hydrogen and R₁ and R₂ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or R₁ and R₉, and R₂ and R₁₁ each, together with the interjacent carbon and nitrogen atoms, form an optionally substituted ring having between 5 and 7 ring atoms; and either R₁₀ and R₁₂ are both hydrogen and R₃ and R₄ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or R₃ and R₁₂, and R₄ and R₁₀ each, together with the interjacent carbon and nitrogen atoms, form an optionally substituted ring having between 5 and 7 ring atoms.

7. The device of claim 6 wherein the metal is zinc.

8. The device of claim 1 wherein the luminescent layer comprises a compound of formula [II]:

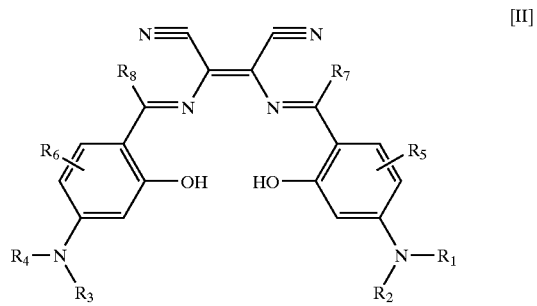

[II]

or a metal complex equivalent thereof.

9. The device of claim 8 wherein $R_1$ to $R_4$ are selected from the group consisting of hydrogen, alkyl, aryl and haloalkyl.

10. An organic electroluminescence device comprising an anode, a cathode, a luminescent layer, at least one hole-transporting layer disposed between said anode and said luminescent layer, at least one electron-transporting layer disposed between said cathode and said luminescent layer, and a substrate present on either the anode or cathode, wherein the luminescent layer comprises a compound of formula [II]:

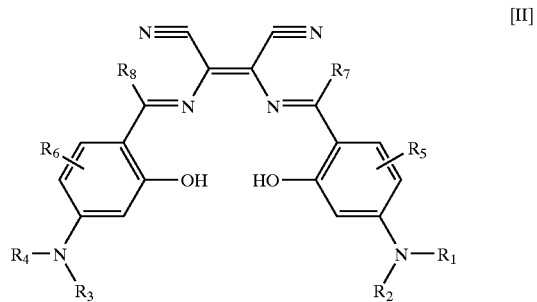

[II]

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups;

wherein $R_1$ to $R_4$ are all hydrogen atoms;

or a metal complex equivalent thereof.

11. The device of claim 8 wherein $R_5$ to $R_8$ are selected from the group consisting of hydrogen, alkyl, alkoxy, aryl, aryloxy and haloalkyl, with the proviso that $R_7$ and $R_8$ are not both hydrogen atoms.

12. The device of claim 11 wherein $R_5$ and $R_6$ are hydrogen atoms, and either $R_7$ or $R_8$ is a hydrogen atom.

13. An organic electroluminescence device comprising an anode, a cathode, a luminescent layer, at least one hole-transporting layer disposed between said anode and said luminescent layer, at least one electron-transporting layer disposed between said cathode and said luminescent layer, and a substrate present on either the anode or cathode, wherein the luminescent layer comprises a compound of formula [III]:

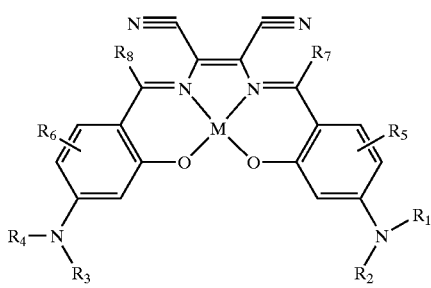

wherein M represents a metal atom;

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups; and $R_1$–$R_4$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups.

14. The device of claim 13 wherein $R_5$ to $R_8$ are selected from the group consisting of hydrogen, alkyl, aryl and haloalkyl.

15. The device of claim 14 wherein $R_5$ to $R_8$ are all hydrogen atoms.

16. An organic electroluminescence device comprising an anode, a cathode, a luminescent layer, at least one hole-transporting layer disposed between said anode and said luminescent layer, at least one electron-transporting layer disposed between said cathode and said luminescent layer, and a substrate present on either the anode or cathode, wherein the luminescent layer comprises a compound of formula [I]:

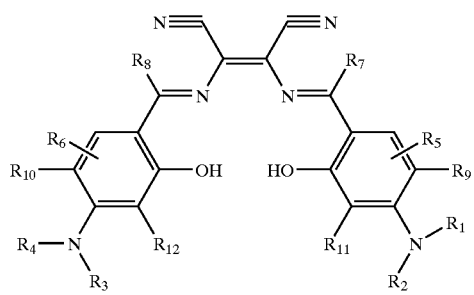

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups; and wherein $R_1$ and $R_9$, $R_2$ and $R_{11}$, $R_3$ and $R_{12}$, and $R_4$ and $R_{10}$ each, together with the interjacent carbon and nitrogen atoms, form an optionally substituted 6-membered ring;

or a metal complex equivalent thereof.

17. The device of claim 16 wherein the 6-membered ring is substituted by at least two $C_1$–$C_4$ alkyl groups.

18. The device of claim 17 wherein the luminescent layer comprises a compound of formula [IV]:

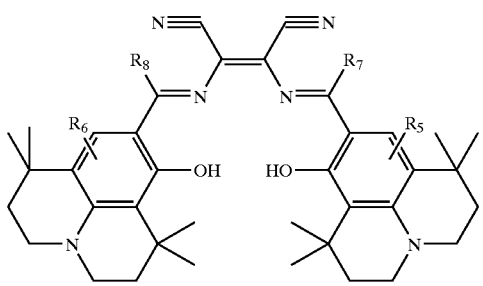

or a metal complex equivalent thereof.

19. The device of claim 18 wherein the luminescent layer comprises a compound of formula [V]:

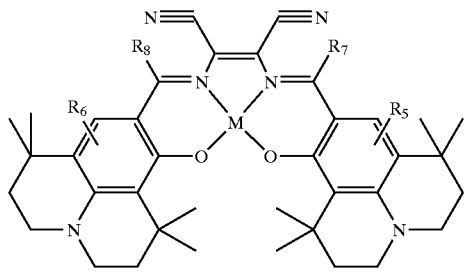

wherein M represents a metal atom.

20. The device of claim 18 wherein $R_5$ to $R_8$ are selected from the group consisting of hydrogen, alkyl, haloalkyl, aryl, aryloxy and alkoxy.

21. The device of claim 20 wherein $R_5$ to $R_8$ are all hydrogen atoms.

22. A method of using a compound of formula [I] in an electroluminescence device:

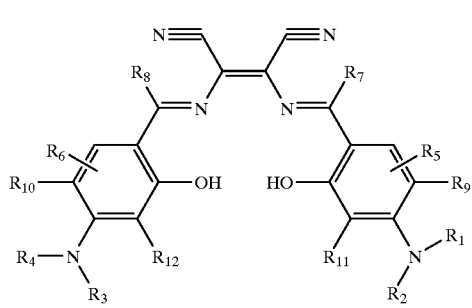

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, with the proviso that $R_7$ and $R_8$ in formula [I] are not both hydrogen atoms;

either $R_9$ and $R_{11}$ are both hydrogen and $R_1$ and $R_2$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_1$ and $R_9$, and $R_2$ and $R_{11}$ each, together with the interjacent carbon and nitrogen atoms, form an optionally substituted ring having between 5 and 7 ring atoms; and either $R_{10}$ and $_{12}$ are both hydrogen and $R_3$ and $R_4$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_3$ and $R_{12}$, and $R_4$ and $R_{10}$ each, together with the interjacent carbon and nitrogen atoms, form an optionally substituted ring having between 5 and 7 ring atoms; or a metal complex equivalent thereof, the method comprising providing a compound of formula [I], and incorporating said compound as a luminescent material within an electroluminescence device which further comprises an anode, a cathode, a hole-transporting layer and an electron-transporting layer.

23. A compound of formula [I]:

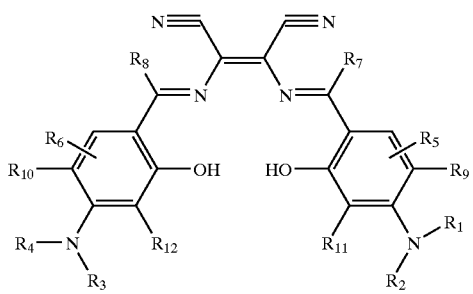

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, with the proviso that $R_7$ and $R_8$ in formula [I] are not both hydrogen atoms;

either $R_9$ and $R_{11}$ are both hydrogen and $R_1$ and $R_2$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_1$ and $R_9$, and $R_2$ and $R_{11}$ each, together with the interjacent carbon and nitrogen atoms, form an optionally substituted ring having between 5 and 7 ring atoms; and either $R_{10}$ and $R_{12}$ are both hydrogen and $R_3$ and $R_4$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_3$ and $R_{12}$, and $R_4$ and $R_{10}$ each, together with the interjacent carbon and nitrogen atoms, form an optionally substituted ring having between 5 and 7 ring atoms;

or a metal complex equivalent thereof.

24. The compound of claim 23 when present as its metal complex equivalent, with the metal being selected from the group consisting of Mg, Ca, Ba, Cr, Fe, Co, Ni, Cu and Zn.

25. A compound of formula [I] present as its metal complex equivalent, wherein the metal is zinc:

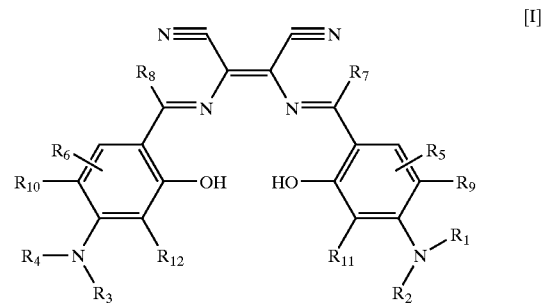

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups;

either $R_9$ and $R_{11}$ are both hydrogen and $R_1$ and $R_2$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_1$ and $R_9$, and $R_2$ and $R_{11}$ each, together with the interjacent carbon and nitrogen atoms, form an optionally substituted ring having between 5 and 7 ring atoms; and either $R_{10}$ and $R_{12}$ are both hydrogen and $R_3$ and $R_4$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups, or $R_3$ and $R_{12}$, and $R_4$ and $R_{10}$ each, together with the interjacent carbon and nitrogen atoms, form an optionally substituted ring having between 5 and 7 ring atoms;

with the proviso that the compound of formula [I] is not the zinc complex of 2,3-bis-[[(2-hydroxy-4-diethylamino)phenyl](methylene)]-amino]-2-butenedinitrile.

26. The compound of claim 23 wherein the compound is of formula [II]:

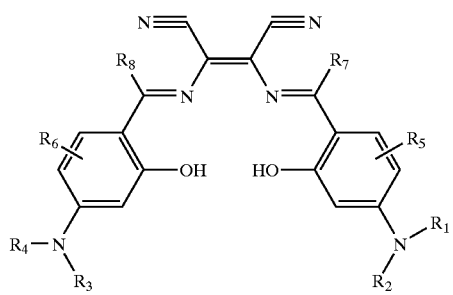

or a metal complex equivalent thereof.

27. The compound of claim 26 wherein $R_1$ to $R_4$ are selected from the group consisting of hydrogen, alkyl, aryl and haloalkyl.

28. The compound of claim 27 wherein $R_1$ to $R_4$ are all hydrogen atoms.

29. The compound of claim 26 wherein $R_5$ to $R_8$ are selected from the group consisting of hydrogen, alkyl, alkoxy, aryl, aryloxy and haloalkyl, with the proviso that $R_7$ and $R_8$ in formula [II] are not both hydrogen atoms.

30. The compound of claim 29 wherein $R_5$ and $R_6$ are hydrogen atoms, and either $R_7$ or $R_8$ in formula [II] is a hydrogen atom.

31. The compound of claim 26 wherein the compound is of formula [III]:

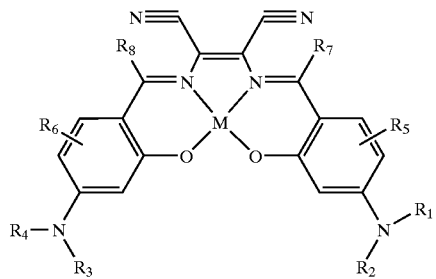

wherein M represents a metal atom.

32. The compound of claim 31 wherein $R_5$ to $R_8$ are selected from the group consisting of hydrogen, alkyl, aryl and haloalkyl, with the proviso that $R_7$ and $R_8$ in formula [III] are not both hydrogen atoms.

33. The compound of claim 32 wherein $R_5$ and $R_6$ are hydrogen atoms, and either $R_7$ or $R_8$ in formula [III] is a hydrogen atom.

34. A compound of formula [I]:

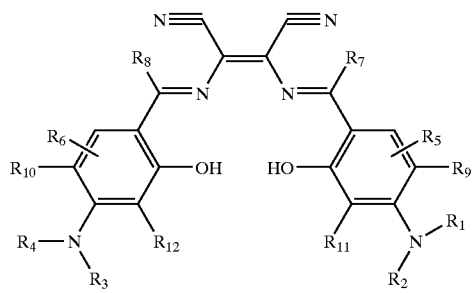

wherein $R_5$–$R_8$ are independently selected from the group consisting of hydrogen and halogen atoms, hydroxy, cyano, nitro, mercapto, carbonyl and sulfone groups, and optionally substituted alkyl, haloalkyl, hydroxyalkyl, aryl, alkoxy, aryloxy, alkylamino, arylamino, alkylarylamino, alkylthio, arylthio, ester, siloxy, cyclic hydrocarbon or heterocyclic groups; and wherein $R_1$ and $R_9$, $R_2$ and $R_{11}$, $R_3$ and $R_{12}$, and $R_4$ and $R_{10}$ each, together with the interjacent carbon and nitrogen atoms, form an optionally substituted 6-membered ring;

or a metal complex equivalent thereof.

35. The compound of claim 34 wherein the 6-membered ring is substituted by at least two $C_1$–$C_4$ alkyl groups.

36. The compound of claim 35 wherein the compound is of formula [IV]:

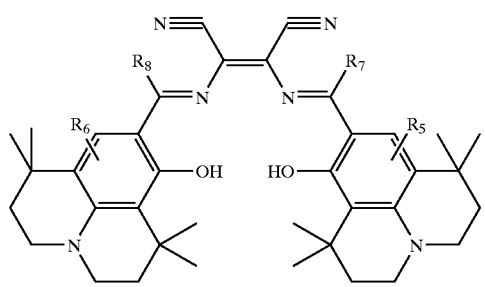

or a metal equivalent thereof.

37. The compound of claim 36 wherein the compound is of formula [V]:

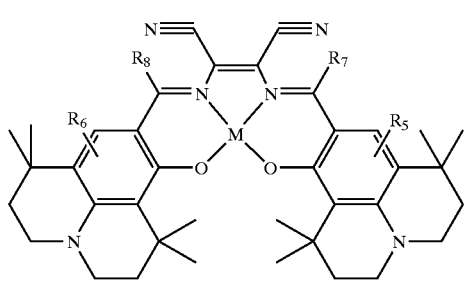

wherein M represents a metal atom.

38. The compound of claim 36 wherein $R_5$ to $R_8$ are selected from the group consisting of hydrogen, alkyl, haloalkyl, aryl, aryloxy and alkoxy.

39. The compound of claim 38 wherein $R_5$ to $R_8$ are all hydrogen atoms.

* * * * *